(12) United States Patent
Trophardy et al.

(10) Patent No.: US 7,846,481 B2
(45) Date of Patent: Dec. 7, 2010

(54) PERFUMING OR FLAVOURING MICROCAPSULES COMPRISING AN EXPLOSION SUPPRESSANT

(75) Inventors: Gil Trophardy, Gex (FR); Glenn Paul Johannes Verhovnik, Chene-Bougeries (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/691,196

(22) Filed: Mar. 26, 2007

(65) Prior Publication Data
US 2007/0190091 A1    Aug. 16, 2007

Related U.S. Application Data

(63) Continuation of application No. PCT/IB2005/053089, filed on Sep. 20, 2005.

(30) Foreign Application Priority Data
Oct. 1, 2004    (EP)    ................... 04104835

(51) Int. Cl.
*A61K 8/11* (2006.01)

(52) U.S. Cl. .......................... 424/489; 512/4

(58) Field of Classification Search ........................ None
See application file for complete search history.

(56) References Cited

U.S. PATENT DOCUMENTS

| | | | |
|---|---|---|---|
| 5,013,473 A | 5/1991 | Norbury et al. | |
| 5,057,328 A * | 10/1991 | Cherukuri et al. | 426/5 |
| 5,922,331 A | 7/1999 | Mausner | |
| 6,056,949 A | 5/2000 | Menzi et al. | |
| 6,153,220 A * | 11/2000 | Cumming et al. | 424/464 |
| 6,514,524 B1 * | 2/2003 | Saslawski et al. | 424/450 |
| 2002/0061831 A1 * | 5/2002 | Kaziska et al. | 510/446 |
| 2004/0022821 A1 * | 2/2004 | Holzner et al. | 424/401 |
| 2004/0208930 A1 * | 10/2004 | Yoneda et al. | 424/470 |
| 2006/0062844 A1 * | 3/2006 | Chenevier et al. | 424/464 |

FOREIGN PATENT DOCUMENTS

| | | |
|---|---|---|
| EP | 0 070 719 | 1/1983 |
| WO | WO 99/65458 * | 12/1999 |
| WO | WO 02062320 A1 * | 8/2002 |
| WO | WO 03/015758 * | 2/2003 |
| WO | WO 03/043728 A1 | 5/2003 |
| WO | WO 2004/066974 * | 8/2004 |

OTHER PUBLICATIONS

Fuentes et al. Psychopharmacology, 59, p. 65-69, 1978.*

* cited by examiner

*Primary Examiner*—Michael G Hartley
*Assistant Examiner*—Nissa M Westerberg
(74) *Attorney, Agent, or Firm*—Winston & Strawn LLP

(57) ABSTRACT

Perfuming or flavoring microcapsules that include, further to a perfuming or flavoring ingredient and a carrier material, an explosion suppressant, proved to undergo, when suspended in hot air during their preparation, an explosion of a reduced violence. The explosion suppressant is selected from $C_1$ to $C_{12}$ carboxylic acids, their salts and mixtures of these.

13 Claims, No Drawings

PERFUMING OR FLAVOURING MICROCAPSULES COMPRISING AN EXPLOSION SUPPRESSANT

CROSS-REFERENCE TO RELATED APPLICATIONS

This application is a continuation of International application PCT/IB2005/053089 filed Sep. 20, 2005, the entire content of which is expressly incorporated herein by reference thereto.

TECHNICAL FIELD

The present invention relates to the field of perfumery and to the flavor industry. It concerns more particularly perfuming or flavoring microcapsules characterized by the fact that, when subjected to a sufficiently powerful ignition source, their rapid combustion reaction is weak or moderate. In fact, the microcapsules of the invention comprise an effective amount of a explosion suppressant susceptible of reducing the violence of their explosion, so as to classify these particles in a dust hazard class St-1.

BACKGROUND OF THE INVENTION

Microcapsules are employed to a large extent in the perfumery and flavoring industries. They constitute delivery systems for perfuming or flavoring ingredients and can be advantageously used in a very large number of applications. The encapsulation of active substances such as perfuming or flavoring ingredients provides at the same time a protection of the ingredients there-encapsulated against "aggressions" such as oxidation or moisture and allows, on the other hand, a certain control of the kinetics of flavor or fragrance release to induce sensory effects through sequential release.

Now, the numerous advantageous properties of microcapsules in these fields are opposed to other properties that must be taken into account during their preparation, transportation, storage and handling. In fact, such delivery systems, due to their nature, and in particular to the fact that they encapsulate volatile and flammable substances, constitute combustible dusts which can, when dispersed in air or another oxygen-containing gas, form readily ignitable mixtures. When ignited by a sufficient powerful ignition source, the result is a rapid combustion reaction with advancing pressure and flame front.

This issue becomes important during the preparation of microcapsules. In particular, spray-drying and fluidized-bed encapsulation processes are highly concerned by this issue, as they are both based on the use of an equipment wherein particles are suspended in hot air as fine particles and can therefore undergo explosion during their preparation.

Spray-drying is the most common encapsulation technique used to stabilize volatile substances such as flavors or fragrances, by encapsulating them in a solid form, suited to many applications. Spray-dried powders are commonly made in an usual spray-drying equipment. Spray-drying is usually effected by means of a rotating disc or of multi-component nozzles. Detailed techniques are described for instance in K. Masters, Spray-drying Handbook, Longman Scientific and Technical, 1991.

Fluidized beds are used for spraying a coating on a core material fluidized in a bed, or agglomerating and/or granulating powders. This encapsulation technique is also well known and is described for instance in EP 70719 or in U.S. Pat. No. 6,056,949, the contents of each of which are expressly included herein by reference thereto.

Both the above-described encapsulation equipments being susceptible to explosions of particles suspended in the air, they thus have to be adapted as a function of the technical safety parameters characterizing the particles there-treated. In particular, they have to be dimensioned as a function of the violence of explosions that can occur during the preparation of microcapsules. Therefore, the problem of reducing the violence of possible explosions of powder products resulting from such encapsulation processes is of paramount importance for the industry.

For the safe handling of combustible substances, it is imperative to know the dangerous properties of a product. The reliable way to characterize the combustible and explosive properties of a product is to subject a sample of the product to various tests and classify the results in accordance with the technical safety characteristics. The international standards (VDI Guideline 2263 part 1: Dust Fires and Dust Explosions, Hazard Assessment-Protective Measures, Test Methods for the Determination of Safety Characteristics of Dusts, Beuth, Berlin, May 1990) describe the test equipments (Modified Hartmann apparatus and Close apparatus, 20-litre sphere apparatus) and methods, namely the ISO standard procedure ISO 6184/1. These methods allow to determine physical constants such as the maximum explosion behavior of a combustible dust in a closed system. A pyrotechnic igniter with a total energy of 10 kJ is used as ignition source. From test methods described in the mentioned guidelines, a characteristic constant, $K_{St}$, which is dust specific is determined. As there are so many such dusts produced and processed in industrial practice, for example for pharmaceutical and cereal, flour products, it is appropriate to assign this maximum explosion constant to one of the several dust explosion classes and to use these as a basis for the dimensioning of constructional protective measures. The correspondence between these classes hereafter referred as dust hazard classes, and the constant $K_{St}$ is the following:

| Dust Hazard Class | Product Specific Constant $K_{St}$ [bar · m · s$^{-1}$] |
|---|---|
| St-1 | 0 to 199 |
| St-2 | 200 to 299 |
| St-3 | ≧300 |

Now, although some perfuming and flavoring ingredients are classified in a dust hazard class St-1, a large number of these ingredients and thus the microcapsules encapsulating them, and depending on the volatility of the perfuming or flavoring ingredients, are still classified under an St-2 dust hazard class and thus require production equipments specifically adapted to the violence of possible explosions, which of course can be very costly.

WO 03/043728 A1 (FIRMENICH) discloses perfuming or flavoring microcapsules having fireproofing agents dispersed in or absorbed within a polymeric carrier material, whereby these fireproofing agents were basically inorganic salts.

In view of these fireproofing agents, other agents suitable as explosion suppressants having further beneficial properties are needed. There is in particular a need of finding more efficient fireproofing agents, which can be used with similar efficiency in smaller amounts, and there is a need of fireproofing agents that have a beneficial effect on the hygroscopicity of the perfuming or flavoring microcapsules, notably it would be an advantage to have a fireproofing agent that reduces hygroscopicity of the perfuming or flavoring microcapsules if compared to fireproofing agents of the prior art. In addition, the fireproofing agents disclosed in WO 03/043728 are not always suitable for use in food applications and other solutions have thus to be found.

The present invention now satisfies these needs.

SUMMARY OF THE INVENTION

Remarkably, we have been able to establish that new explosion suppressants being $C_1$-$C_{12}$ carboxylic acids, salts of $C_1$-$C_{12}$ carboxylic acids, and mixtures thereof could be added directly to perfuming and flavoring microcapsules in an amount effective to reduce the violence of possible explosions during their preparation, in particular when suspended in hot air. The $K_{St}$ constant of microcapsules comprising the new explosion suppressants could thus be effectively reduced. Very surprisingly, these new explosion suppressants also reduce the hygroscopicity of powders comprising the microcapsules of the present invention.

Therefore, in a first aspect, the present invention provides perfuming or flavoring microcapsule comprising at least one perfuming or flavoring ingredient dispersed in or adsorbed within a polymeric carrier material, characterized in that the microcapsule further comprises an effective amount of a explosion suppressant selected from the group of $C_1$-$C_{12}$ carboxylic acids, salts of $C_1$-$C_{12}$ carboxylic acids, and mixtures thereof.

In a second aspect, the present invention provides methods for the preparation of perfuming or flavoring compositions according to the invention.

In a further aspect, the present invention provides the use of a explosion suppressant selected from the group consisting of $C_1$-$C_{12}$ carboxylic acids, salts of $C_1$-$C_{12}$ carboxylic acids, and mixtures thereof in the composition of a microcapsule for reducing the violence of the explosion of the microcapsule.

In a still further aspect, the present invention provides a method for reducing explosivity of a powdered composition, the method comprising the step of adding to the powdered composition a fireproof agent selected from the group consisting of $C_1$-$C_{12}$ carboxylic acids, salts of $C_1$-$C_{12}$ carboxylic acids, and mixtures thereof to the powdered composition, and/or, incorporating the fire proof in and/or within particles of the powdered composition, and/or, coating the fire proof agent onto the powdered composition.

Furthermore, the present invention provides perfumed product and a food, beverage or pharmaceutical product, characterized in that it comprises the flavoring and/or perfuming microcapsule of the present invention.

DETAILED DESCRIPTION OF THE PREFERRED EMBODIMENTS

As mentioned above, the St-class of a microcapsule is deduced from the value of its product specific constant $K_{St}$ (see correspondence Table above). The $K_{St}$ parameter is measured by means of the ISO standard procedure ISO 6184/1 in a 20l sphere apparatus. This equipment and the methods of measurement of $K_{St}$ are described in International standards, hereby included by reference (VDI Guideline 2263 part 1: Dust Fires and Dust Explosions, Hazard Assessment-Protective Measures, Test Methods for the Determination of Safety Characteristics of Dusts, Beuth, Berlin, May 1990).

The perfuming or flavoring microcapsules of the invention comprise an effective amount of a explosion suppressant which is capable of reducing the violence of the explosion of the microcapsules possibly induced by their suspension in the air during their preparation. This is very advantageous considering that such delivery systems are mainly composed of highly volatile ingredients which constitute therefore combustible dusts. Such volatile ingredients had to be used in the past in limited proportions in compositions subjected to processes involving the suspension of particles in hot air. Now, the solution provided by the present invention allows to use higher quantities of these ingredients, and therefore provides an advantageous alternative to the prior use of precursors of certain particularly volatile ingredients.

The invention therefore provides an advantageous solution as regards the problem of the preparation of perfuming and flavoring microcapsules and powder products, in particular for preparations via processes involving a spray-drier or a fluidized bed, wherein fine particles are suspended in the air and are therefore more susceptible of exploding. Under an St-1 class, the violence of the explosion will be a weak or at least moderate reaction, whereas it would be a strong reaction for a dust hazard class St-2, and a very strong reaction for a dust hazard class St-3. As a consequence, the equipment used for the preparation of microcapsules according to the present invention can be dimensioned accordingly i.e. as St-1 and thus become less costly, whilst guarantying the same or better manufacture safety conditions.

The term $C_1$-$C_{12}$ carboxylic acids refers to carboxylic acids that have 1 to 12 carbon atoms, including the C-atom of the carboxyl group. Therefore, if more than one carboxylic group are present in the carboxylic acid of the present invention, these further carboxylic group are, equally, to be counted to the 1 to 12 carbon atoms of the carboxylic acid used as a explosion suppressant according to the present invention.

Preferably, the carboxylic acids and/or their salts that are used as explosion suppressants in microcapsules of the present invention are linear, branched, cyclic, and/or aromatic carboxylic acids and/or their salts. The carboxylic acids may be saturated hydrocarbons. Alternatively, the carboxylic acids may be unsaturated hydrocarbons.

Examples of cyclic carboxylic acids are lactones, for example ascorbic acid. An example for an aromatic carboxylic acid is salicylic acid.

Preferably, the carboxylic acids and/or their salts are functionalized hydrocarbon carboxylic acids and/or their salts.

Preferably, the carboxylic acid comprise less than 7, more preferably less than 5 and most preferably less than 3 carbon atoms covalently bound to 2 hydrogen atoms.

Preferably, the carboxylic acid of the present invention comprises 5 or less carbon atoms with an oxidation number of (-II) or more negative. More preferably, the carboxylic acid comprises 3 or less carbon atoms having a oxidation number of (-II) or more negative.

In an embodiment of the present invention, the carboxylic acids and/or their salts are hydroxy- and/or keto-functionalised hydrocarbon carboxylic acids and/or their salts. Preferably, the carboxylic acid of the present invention comprises at least 1 hydroxy group. Preferably, it comprises at least 2 hydroxy groups.

In a further embodiment of the microcapsules of the present invention, the carboxylic acids and/or their salts are di-, tri-, or multi carboxylic acids and/or their salts. Examples of multi carboxylic acids include citric acid, which is $C_6$-tricarboxylic acid.

Preferably, the carboxylic acid is at least a di carboxylic acid. More preferably, it is at least a tri carboxylic acid, meaning that it carries at least three carboxylic groups.

Preferably, the carboxylic acid and/or their salt is a $C_4$-$C_8$ carboxylic acid and/or their salt.

In a preferred embodiment of the present invention, the carboxylic acid and/or their salts are selected from $C_2$-$C_6$ carboxylic acids and/or their salts.

In an embodiment of the perfuming or flavoring microcapsule of the present invention, the carboxylic acid and/or its salt is selected from the group consisting of acetic acid, propionic acid, butyric acid, isobutyric acid, valeric acid, caproic acid, citric acid, succinic acid, hydroxysuccinic acid, maleic acid, fumaric acid, oxylic acid, glyoxylic acid, adipic acid, lactic acid, lactic acid, tartric acid, salicylic acid, ascorbic acid the potassium, calcium and/or sodium salts of any of the fore-mentioned acid, and mixtures of any of these.

Preferably, the salts of the carboxylic acids are potassium and/or sodium salts. More preferably, it is the tripotassium and/or trisodium salt of a tricarboxylic acid. Most preferably, it is the tripotassium and/or trisodium salt of citric acid.

The above acids and their salts are commercially available and their synthesis, or isolation from raw materials, is known to the skilled person.

In an embodiment of the present invention, the microcapsule comprises from 0.5 to 80% by weight of explosion suppressant relative to the dry weight of the microcapsule. Preferably, the microcapsule comprises 1 to 40%, more preferably 2 to 20%, and most preferably 2 to 10% by weight of explosion suppressant relative to the dry weight of the microcapsule.

The microcapsule of the invention is based on the presence of at least one perfuming or flavoring material and a polymeric carrier material.

The perfuming or flavoring ingredient, in the form of one sole ingredient or in the form of a composition, either in isolation or, optionally, in a solution or suspension in solvents and adjuvants of current use, represents from 1 to 70%, and preferably from 15 to 60%, most preferably 20 to 45% by weight relative to the total weight of the microcapsule.

The terms perfume or flavor ingredient or composition as used herein are deemed to define a variety of fragrance and flavor materials of both natural and synthetic origins. They include single compounds and mixtures. Specific examples of such components may be found in the current literature, e.g. in Perfume and Flavor Chemicals by S. Arctander, Montclair, N.J. (USA); Fenaroli's Handbook of Flavor Ingredients, CRC Press or Synthetic Food Adjuncts by M. B. Jacobs, van Nostrand Co. Inc., and other similar text books; and are well-known to the person skilled in the art of perfuming, flavoring and/or aromatising consumer products, i.e. of imparting an odor or a taste to a consumer product.

According to the present invention, the perfume or flavor ingredient or composition is dispersed in, coated onto or absorbed in a carrier material.

Preferably, the carrier material comprises carbohydrates. For example, the carrier material comprise mono-, oligo- and/or polysaccharides, wherein the prefixes oligo- and poly are as defined below.

In an embodiment of the present invention, the carrier material comprises a monomeric, oligomeric or polymeric carrier material, or mixtures of two or more of these. An oligomeric carrier is a carrier wherein 2-10 monomeric units are linked by covalent bonds. For example, if the oligomeric carrier is a carbohydrate, the oligomeric carrier may be sucrose, lactose, raffinose, maltose, trehalose, fructo-oligosaccharides, to name a few examples only.

Examples of a monomeric carrier materials are glucose, fructose, mannose, galactose, arabinose, fucose, sorbitol, mannitol, for example.

Polymeric carriers have more than 10 monomeric units that are linked by covalent bonds. Non limiting examples of the latter include polyvinyl acetate, polyvinyl alcohol, dextrines, maltodextrines, natural or modified starch, vegetable gums, pectins, xanthanes, alginates, carragenans or yet cellulose derivatives such as for example carboxymethyl cellulose, methylcellulose or hydroxyethylcellulose, and generally all materials currently used for encapsulation of volatile substances. Preferably, the polymeric carrier comprises maltodextrin. Most preferably it comprises maltodextrin and modified starch, such as, for example, alkenyl-succinated starch.

In another embodiment, the perfume or flavor ingredient or composition is adsorbed within a polymeric carrier material. As non limiting examples of the latter, one can cite amorphous silica, precipitated silica, fumed silica and aluminosilicates such as zeolite and alumina.

According to an aspect, the present invention provides methods for the preparation of perfuming and flavoring microcapsules comprising a explosion suppressant. There are several alternatives to the method for the preparation of the microcapsules of the invention. In a first embodiment, the explosion suppressant is added to an aqueous emulsion consisting of the perfuming or flavoring ingredient or composition dispersed in the polymeric carrier material. The obtained emulsion is then spray-dried in order to form a powder. Optionally, an emulsifier may be added to the initial emulsion. This encapsulation technique does not require a more detailed description herein, as it relies on conventional spray-drying techniques, which are perfectly well documented in the prior art [see for example Spray-Drying Handbook, $3^{rd}$ ed., K. Masters; John Wiley (1979)] and currently applied in the food industry or in the flavor and perfume industries.

In another embodiment, the explosion suppressant, in the form of a solid powder, is simply blended with a spray-dried powder formed from the aqueous emulsion of perfuming or flavoring ingredient or composition in the polymeric carrier material and the emulsifier.

A third alternative for the preparation of the microcapsules of the invention presenting an explosion reaction of reduced violence, is to firstly adsorb the perfuming or flavoring ingredient or composition within a porous polymeric carrier material as described above and to further coat the resulting system with a explosion suppressant. This method of preparation can be carried out in a fluidized bed apparatus, according to conventional techniques such as those described for instance in EP 70719 or in U.S. Pat. No. 6,056,949 the contents of which are hereby included by reference. The particles formed by adsorption of a fragrance or flavor ingredient or composition within the carrier can thus be coated after granulation, e.g. by spraying a solution, emulsion or melt of the explosion suppressant, which forms a protective film around the core.

During the granulation process, there can also be used usual additives such as artificial sweeteners, food dyes, vitamins, antioxidants, anti-foam agents, carbonic acid generators, or additional flavorants etc. which can be added to the core material or to the spray emulsion.

The microcapsules of the invention have an average diameter varying from usually 5 to 800 µm, more preferably 50 to 300 µm.

In an aspect, the present invention provides a method for reducing violence of explosion of a powdered composition. The composition is preferably a perfuming or flavoring composition. More preferably, it is a composition comprising flavoring perfuming and/or perfuming microcapsules. Violence of explosion is determined by the $K_{St}$ constant described above. The adding of the explosion suppressant to a powdered composition may be performed by adding to a spray-dried powdered. However, any way of dry- or wet-adding the explosion suppressant to a powdered composition is encompassed. For example, the adding is a dry-blending or dry-mixing with the components of the powdered composition. Alternatively, the explosion suppressant may be incorporated in and/or within the particles of a powdered composition. This step may be performed by adding the explosion suppressant to an aqueous emulsion dispersed in a polymeric carrier material as described above, followed by drying the obtained emulsion, for example by spray drying.

In a further alternative, the explosion suppressant may simply be coated onto a powdered composition. The coating may be performed by coating onto a porous polymeric carrier material, for example with a fluidized bed apparatus, as discussed above, for example.

The microcapsules of the invention can advantageously be used to impart, improve, enhance or modify the organoleptic properties of a great variety of edible or perfumed end products. In the field of perfumery, the perfuming microcapsules resulting from any embodiment of the process according to the invention can be incorporated in a perfuming composition such as a perfume, a Cologne or an after-shave lotion, or yet they can be added to functional products such as detergents or fabric softeners, soaps, bath or shower gels, deodorants, body lotions, shampoos and other hair-care products, household cleansers, cleaning and deodorizing blocks for toilet tanks. On the other hand, in the case of flavors encapsulated, the consumer products susceptible of being flavored by the microcapsules of the invention may include foods, beverages, pharmaceuticals and the like.

The concentrations in which the microcapsules of the invention can be incorporated in such consumer products vary in a wide range of values, which are dependent on the nature of the product to be perfumed or flavored. Typical concentrations, to be taken strictly by way of example, are comprised in a range of values as wide as from a few ppm up to 5 or 10% of the weight of the flavoring or perfuming composition or finished consumer product into which they are included.

The invention will be now illustrated but not limited by way of the following examples wherein temperatures are given in degrees centigrade and abbreviations have the meaning common in the art.

EXAMPLES

Examples 1-9

Spray-Drying of a Perfuming Emulsions Comprising a Explosion Supressant

Nine perfuming emulsions were prepared based on different compositions given in Table 1 below (parts by weight). The compositions are based on two different perfuming compositions (perfume A and perfume B), whereby different explosion suppressants were compared:

| Example | Explosion suppressant |
|---|---|
| 1 and 2 | $Na_3$ citrate |
| 3 and 4 | Citric acid |
| 5 and 6 | $K_3$ citrate |
| 7 and 8 | $NaH_2PO_4$ (prior art) |
| 9 | none (control) |

In Examples 1-9 given in Table 1, stabilizers were first dissolved in the perfume. The remaining ingredients were homogenized with an equivalent amount of water and then the perfume was emulsified in this dispersion by means of a Silverstone type fast stirrer. The mixtures were then spray dried in a Sodeva apparatus with an emulsion output of 2 kg/h, drying air: 320 $m^3$/h at 350° C. and $0.45 \times 10^5$ Pa.

There were thus obtained 9 fine powders comprising microcapsules, the diameter of the microcapsules being comprised between 10 and 100 µm and the content of liquid perfume being 36-40% by weight.

The explosive character of the powders was measured with a 20 l sphere apparatus (see VDI Guideline 2263 part 1: Dust Fires and Dust Explosions, Hazard Assessment-Protective Measures, Test Methods for the Determination of Safety Characteristics of Dusts, ISO standard procedure ISO 6184/1, Beuth, Berlin, May 1990), and the powders were attributed dust hazard classes St-1 (Examples 1-8, comprising fireproof agents), and St-2-3 (Example 9, no fireproof agent), see details in Table 1.

From Table 1 it can be seen that citric acid, sodium and potassium citrate effectively reduced explosive violence of the microcapsules. The most effective explosion suppressant was potassium citrate, which was added at 5% of the composition and which reduced explosivity to 119 Kst (perfume B) and 132 Kst (perfume A), respectively. Potassium citrate had thus the same, or even better reducing effect on violence of explosion than the explosion suppressant of the prior art (WO 03/043728), mono-sodium phosphate, which was used at much higher concentrations (15wt.-%, Example 9).

In conclusion, the new explosion suppressants of the present invention can reduce the violence of explosion of perfuming microcapsules and are effective at substantially lower concentration than explosion suppressant used in similar compositions from the prior art.

Example 10

Hygroscopy of New Explosion Suppressants in Comparison with the Prior Art

Hygroscopicity (the tendency to absorb water) of the microcapsules of Examples 5 (present invention) and 7 (prior art) is determined in a Dynamic Vapor Sorption, commercialized by Surface Measurements Systems Ltd, 3 Warple Mews, Warple Way, London, W3 ORF, at increasing relative humidity (40%, 50%, 60%, 70%, 80%) to determine the "melting" point of the two powders at 30° C. The "melting point", in the context of the present Example 10, refers to the relative humidity at which a powder has absorbed so much water that it loses its powdery aspect and starts to flow like a liquid, that is, it "melts". The specific relative humidity at which this happens can be determined due to the observation of the powder during the water-absorption from humid air by aid of a camera.

The perfuming microcapsules of Example 5, comprising 5% of potassium citrate "melts" at a relative humidity of 80% RH, while the perfuming powder of Example 7 (prior art) already "melts" at 60% RH. In additional test, a powdered perfuming composition comprising 15% potassium citrate was prepared, which was found to "melt" at 70% RH.

The difference in hygroscopicity in powders comprising microcapsules of the present invention can be attributed, without being bound by theory, first to the fact that potassium citrate leads to less hygroscopicity powders than sodium phosphate. In addition, less of the explosion suppressant needs to be used, which further reduces hygroscopicity of the powder. In conclusion, the present invention surprisingly provides powdered perfuming compositions that withstand very humid environments of up to 80% RH at 30° C.

TABLE 1

Compositions of spray-dried fragrance powders

| Example | 1 | 2 | 3 | 4 | 5 | 6 | 7 | 8 | 9 |
|---|---|---|---|---|---|---|---|---|---|
| Perfume A[1] |  | 40.00 |  | 40.00 |  | 40.00 |  | 40.00 | 40.00 |
| Perfume B[1] | 40.00 |  | 40.00 |  | 40.00 |  | 40.00 |  |  |
| Stabilizers | 1.00 | 1.00 | 1.00 | 1.00 | 1.00 | 1.00 | 1.00 | 1.00 | 1.00 |
| Citric acid | 2.50 | 2.50 | 5.46 | 5.46 | 2.50 | 2.50 | 2.50 | 2.50 | 2.50 |
| Na$_3$ Citrate x 2 H$_2$O | 4.53 | 4.53 |  |  |  |  |  |  |  |
| K$_3$ Citrate x 1 H$_2$O |  |  |  |  | 5.00 | 5.00 |  |  |  |
| NaH$_2$PO$_4$ |  |  |  |  |  |  |  | 15.00 | 15.00 |
| Antifoam agent | 0.10 | 0.10 | 0.10 | 0.10 | 0.10 | 0.10 | 0.10 | 0.10 | 0.10 |
| Capsul[2] | 40.67 | 40.67 | 42.24 | 42.24 |  | 40.20 | 33.20 | 33.20 | 48.20 |
| Further carbohydrates | 11.2 | 11.2 | 11.2 | 11.2 | 11.2 | 11.2 | 9.7 | 9.7 | 9.7 |
| Explosivity class/ KST (bar x m/s) | CLASS 1/ 174 | CLASS 1/ 158 | CLASS 1/ 198 | CLASS 1/ 190 | CLASS 1/ 118 | CLASS 1/ 132 | CLASS 1/ 149 | CLASS 1/ 117 | CLASS 2-3/ >250 |
| Encapsulated perfume | 36.90% | 40.00% | 36.40% | 37.90% | 36.90% | 37.90% | 40.00% | 38.50% | n.d. |

[1] origin: Firmenich S A, Geneva, Switzerland
[2] dextrin dioctenylsuccinate; origin: National Starch, USA Example 11

Based on the composition of the perfuming microcapsules given below, microcapsules are prepared by dry blending a spray dried powder comprising polymeric carrier and a perfuming ingredient with a explosion suppressant in a powdered form.

Dry Blending with Explosion Suppressant

An emulsion of the following composition was spray-dried in a spray-drier Büchi (origin: Switzerland):

| Ingredients | grams |
|---|---|
| Water | 150.0 |
| CAPSUL ®[1] | 67.0 |
| Perfume concentrate[2] | 33.0 |
| Total | 250.0 |

[1] dextrin dioctenylsuccinate; origin: National Starch, USA
[2] origin: Firmenich S A, Geneva, Switzerland The theoretical yield after evaporation of water is of 100 g of powder containing 33% of perfume.

The explosive character of the powder is measured with a 20 l sphere apparatus (see Examples 1-9), and the powder was attributed a dust hazard class St-2.

The same powder is then mixed with potassium citrate (K$_3$ citrate×1 H$_2$O) in a powder form, in a ratio of 85:15.

The analysis of the explosive character of the homogeneous mixture, made under the same condition demonstrated that the mixture is classified as St-1.

What is claimed is:

1. A spray-dried powder of starch microcapsules comprising, as ingredients:
   a carrier material of a starch;
   at least one perfuming ingredient present in an amount which is between 15 and 60% by weight of the microcapsules' dry weight; and
   an explosion suppressant in an amount of 2 to 20% by weight of the microcapsules' dry weight, with the explosion suppressant selected from the group consisting of $C_1$-$C_{12}$ carboxylic acids, salts of $C_1$-$C_{12}$ carboxylic acids, and mixtures thereof, with the explosion suppressant present in an amount to provide the powder with an St-1 dust hazard explosive classification,
   wherein the spray dried powder is obtained by spray drying of an emulsion that includes the ingredients with the explosion suppressant present so that the powder has a reduced tendency to explode when being spray dried from the emulsion.

2. The microcapsules of claim 1, wherein the carboxylic acids or their salts are hydroxy- or ceto-functionalized hydrocarbon carboxylic acids or their salts.

3. The microcapsules of claim 1, wherein the carboxylic acids or their salts are di-, tri-, or multi carboxylic acids or their salts.

4. The microcapsules of claim 1, wherein the carboxylic acid and/or their salts are selected from $C_2$-$C_6$ carboxylic acids or their salts.

5. The microcapsules of claim 1, wherein the carboxylic acid is selected from the group consisting of acetic acid, propionic acid, butyric acid, isobutyric acid, valeric acid, caproic acid, citric acid, succinic acid, hydroxysuccinic acid, maleic acid, fumaric acid, oxylic acid, glyoxylic acid, adipic acid, lactic acid, tartric acid, salicylic acid, ascorbic acid, the potassium, calcium or sodium salts of any of the afore-mentioned acids, and mixtures of any of these.

6. The microcapsules of claim 1, wherein the carboxylic acid is selected from the group consisting of acetic acid, propionic acid, butyric acid, isobutyric acid, valeric acid, caproic acid, succinic acid, hydroxysuccinic acid, maleic acid, fumaric acid, oxylic acid, glyoxylic acid, adipic acid, lactic acid, tartric acid, salicylic acid, ascorbic acid the potassium, calcium or sodium salts of any of the afore-mentioned acids, and mixtures of any of these.

7. The microcapsules of claim 1, wherein the explosion suppressant is potassium citrate.

8. The microcapsules of claim 1, wherein the carrier material comprises maltodextrin.

9. The microcapsules of claim 1, wherein the explosion suppressant is present in an amount of from 2 to 10% by weight relative to the dry weight of the microcapsules.

10. The microcapsules of claim 1, wherein the perfume ingredient is present in an amount of from 20 to 45% by weight relative to the total weight of the microcapsules.

11. A method for reducing violence of explosion of perfuming microcapsules as defined in claim 1, which comprises preparing the microcapsules by incorporating the explosion suppressant in or within the microcapsules.

12. A perfumed product selected from the group consisting of a perfume, a Cologne, an after-shave lotion, a soap, a bath or shower gel, a deodorant, a body lotion, a shampoo or another hair-care product, a detergent, a fabric softener, a household cleaner and a cleaning and deodorizing block for toilet tanks, characterized in that it comprises perfuming microcapsules according to claim 1.

13. A food, beverage or pharmaceutical product, which comprises perfuming microcapsules according to claim 1.

* * * * *